United States Patent
Myodo et al.

(10) Patent No.: US 11,623,813 B2
(45) Date of Patent: Apr. 11, 2023

(54) RESIN COMPOSITION-FILLED SYRINGE, AND PRODUCTION METHOD AND PRESERVATION METHOD FOR SAME

(71) Applicant: NAMICS CORPORATION, Niigata (JP)

(72) Inventors: Hiroki Myodo, Niigata (JP); Masaaki Hoshiyama, Niigata (JP)

(73) Assignee: NAMICS CORPORATION, Niigata (JP)

( * ) Notice: Subject to any disclaimer, the term of this patent is extended or adjusted under 35 U.S.C. 154(b) by 0 days.

(21) Appl. No.: 17/435,198

(22) PCT Filed: Feb. 6, 2020

(86) PCT No.: PCT/JP2020/004650
§ 371 (c)(1),
(2) Date: Aug. 31, 2021

(87) PCT Pub. No.: WO2020/202782
PCT Pub. Date: Oct. 8, 2020

(65) Prior Publication Data
US 2022/0144531 A1 May 12, 2022

(30) Foreign Application Priority Data
Mar. 29, 2019 (JP) .............................. JP2019-067261

(51) Int. Cl.
*B65D 83/00* (2006.01)
(52) U.S. Cl.
CPC ................................ *B65D 83/0022* (2013.01)

(58) Field of Classification Search
CPC .............. B65D 83/0022; B65D 41/005; B65D 83/0033; B65D 83/0044; A61J 3/00; A61M 5/24
See application file for complete search history.

(56) References Cited

U.S. PATENT DOCUMENTS

| 5,607,400 A | * | 3/1997 | Thibault ........... A61M 5/31513 604/218 |
| 6,423,037 B1 | * | 7/2002 | Hijikata ................ A61M 5/178 604/235 |

(Continued)

FOREIGN PATENT DOCUMENTS

| JP | 8-317975 A | 12/1996 |
| JP | 2006-116223 A | 5/2006 |

(Continued)

OTHER PUBLICATIONS

International Search Report (ISR) dated Apr. 14, 2020 filed in PCT/JP2020/004650.

*Primary Examiner* — Bob Zadeh
(74) *Attorney, Agent, or Firm* — Rankin, Hill & Clark LLP

(57) ABSTRACT

There is provided a syringe filled with a resin composition which prevents a barrel cap from being detached due to temperature change during storage or during transportation, a production method thereof, and a storage method thereof. This syringe filled with the resin composition includes a syringe having a syringe barrel, a resin composition filling the syringe barrel, a plunger inserted in the syringe barrel, a barrel cap blocking an opening of the syringe barrel, and a spatial part between the plunger and the barrel cap in the syringe barrel. The pressure of the spatial part in a frozen state is 50 kPa to 92 kPa.

12 Claims, 1 Drawing Sheet

(56) References Cited

U.S. PATENT DOCUMENTS

| | | | | |
|---|---|---|---|---|
| 2011/0282185 A1* | 11/2011 | Yanase | .............. | A61M 5/31513 |
| | | | | 600/420 |
| 2012/0277684 A1* | 11/2012 | Cronenberg | .......... | B65B 7/2821 |
| | | | | 604/206 |
| 2015/0041498 A1* | 2/2015 | Kakiuchi | .................. | A61J 1/20 |
| | | | | 53/471 |
| 2015/0105750 A1* | 4/2015 | Laugharn, Jr. | ...... | A61M 5/3134 |
| | | | | 604/513 |
| 2016/0015900 A1* | 1/2016 | Cronenberg | ........ | A61M 5/2448 |
| | | | | 604/82 |
| 2017/0224935 A1* | 8/2017 | Hoffmann | ................ | A61M 5/46 |
| 2018/0147357 A1* | 5/2018 | Marashi | ............... | A61M 5/285 |
| 2018/0369504 A1* | 12/2018 | Leibovici | ................ | A61C 19/08 |
| 2020/0001011 A1 | 1/2020 | Myodo et al. | | |
| 2022/0144531 A1* | 5/2022 | Myodo | .............. | B65D 83/0022 |

FOREIGN PATENT DOCUMENTS

| | | | | |
|---|---|---|---|---|
| JP | 2012-5509 A | 1/2012 | | |
| WO | WO-2004105825 A1 * | 12/2004 | ............. | A61L 27/46 |
| WO | 2010/146979 | 12/2010 | | |
| WO | 2018/168587 A1 | 9/2018 | | |
| WO | WO-2018168587 A1 * | 9/2018 | .............. | A61M 5/28 |

* cited by examiner

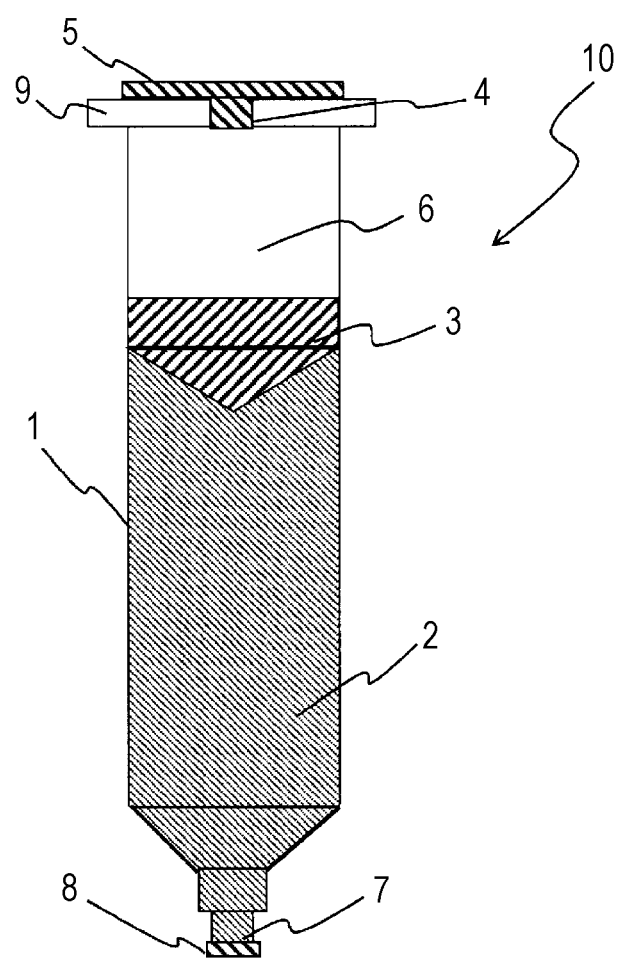

RESIN COMPOSITION-FILLED SYRINGE, AND PRODUCTION METHOD AND PRESERVATION METHOD FOR SAME

TECHNICAL FIELD

The present invention relates to a syringe filled with a resin composition, a production method thereof, and a storage method thereof. In particular, the present invention relates to a syringe filled with a frozen resin composition, a production method thereof, and a storage method thereof.

BACKGROUND ART

A prefilled syringe, in which a syringe is previously filled with a pharmaceutical drug or a pharmaceutical composition, is known. While a prefilled syringe is stored or after it is unpacked, a pharmaceutical drug or a pharmaceutical composition filling a syringe is sometimes mixed with outside air. In that case, dust or dirt may enter together with outside air. Therefore, there are desires for a prefilled syringe which can suppress the entrance of outside air.

For example, in the prefilled syringe disclosed in PATENT LITERATURE 1, a pusher is fitted to a gasket or a plunger of a syringe filled with a pharmaceutical drug or pharmaceutical composition. Furthermore, this prefilled syringe includes: a sealing member having an insertion hole for inserting a pusher into a base end opening of a syringe; and a film constituted by an elastic material as a sealing member disposed to a reduced diameter portion at a leading end of a syringe. In the prefilled syringe disclosed in PATENT LITERATURE 1, a pusher to move a gasket or a plunger is previously fitted to a syringe. This suppresses the entrance of outside air into a syringe barrel when a prefilled syringe is used.

CITATION LIST

Patent Literature

PATENT LITERATURE 1: JP-A-2006-116223

SUMMARY OF INVENTION

Problems to be Solved by Invention

Not only a pharmaceutical drug or a pharmaceutical composition but also a resin composition used in a sealant of mechanical components or electronic components, an adhesive, a paste for forming electrical circuits, and a solder for mounting electronic components are supplied to specific microscopic sites of objects. Therefore, a resin composition is sometimes stored or transported in a state of previously filling a syringe. For maintaining a stable state in which a reaction of a resin composition filling a syringe is suppressed, a syringe filled with a resin composition frozen at 0° C. or lower is sometimes stored or transported. The frozen resin composition is thawed to normal temperature (for example, 25° C.) when in use. However, the volume of air contained in the syringe significantly changes between when frozen at 0° C. or lower and when thawed to room temperature (for example, 25° C.). Accordingly, a barrel cap blocking an opening of a syringe barrel is sometimes detached, which causes foreign substances to be mixed into the syringe.

Therefore, an aspect of the present invention has as its object to provide a syringe filled with a resin composition, in which a barrel cap is prevented from being detached due to temperature change during storage or transportation, a production method thereof, and a storage method thereof.

Solution to Problems

A solution for solving the above-described problems is as follows. That is, the present invention encompasses the following aspects.

[1] A syringe filled with a resin composition which includes: a syringe having a syringe barrel; a resin composition filling the syringe barrel; a plunger inserted into the syringe barrel; a barrel cap blocking an opening of the syringe barrel; and a spatial part between the plunger and the barrel cap in the syringe barrel, in which the pressure of the spatial part in a frozen state is 50 kPa to 92 kPa.

[2] The syringe filled with the resin composition according to [1], in which the filling amount of the resin composition is 10% to 95% of the internal capacity of the syringe.

[3] The syringe filled with the resin composition according to [1] or [2], in which the resin composition contains at least one resin selected from epoxy resin and acrylic resin.

[4] The syringe filled with the resin composition according to any one of [1] to [3], in which the viscosity of the resin composition of less than 200 Pa·s measured at 25° C. and a rotational speed of 50 rpm and the viscosity of the resin composition of 200 Pa·s or more measured at 25° C. and a rotational speed of 10 rpm, using a rotary viscometer, are in a range of 2.5 Pa·s to 650 Pa·s.

[5] The syringe filled with the resin composition according to any one of [1] to [4], in which thixotropic indices TI1 to TI3 of the resin composition measured under any of conditions (1) to (3) below are in a range of 0.4 to 4.0.

(1) Thixotropic index TI1 is a ratio between a viscosity at 5 rpm and a viscosity at 50 rpm, when a viscosity measured at 25° C. and 50 rpm using a rotary viscometer is in a range of not less than 2.5 Pa·s and less than 20 Pa·s.

(2) Thixotropic index TI2 is a ratio between a viscosity at 5 rpm and a viscosity at 50 rpm, when a viscosity measured at 25° C. and 50 rpm using a rotary viscometer is in a range of not less than 20 Pa·s and less than 200 Pa·s.

(3) Thixotropic index TI3 is a ratio between a viscosity at 1 rpm and a viscosity at 10 rpm, when a viscosity measured at 25° C. and 10 rpm using a rotary viscometer is in a range of 200 Pa·s or more and 1,000 Pa·s or less.

[6] The syringe filled with the resin composition according to any one of [1] to [5], in which the syringe is made from polypropylene or polyethylene.

[7] The syringe filled with the resin composition according to any one of [1] to [6], in which the syringe has an internal capacity of 1 $cm^3$ to 600 $cm^3$.

[8] The syringe filled with the resin composition according to any one of [1] to [7], which is used for freezing.

[9] A storage method of a syringe filled with a resin composition, including storing the syringe filled with the resin composition according to any one of [1] to [8] at a temperature of −80° C. to 0° C.

[10] A production method of a syringe filled with a resin composition, including: a step of preparing a syringe filled with a resin composition having a spatial part between a plunger and a barrel cap in a syringe barrel, by filling the syringe barrel having the plunger inserted therein with a resin composition and blocking an opening of the syringe barrel with the barrel cap; a step of freezing the syringe filled with the resin composition at a temperature of −80° C. to 0° C.; and a step of reducing the pressure of the spatial part of the frozen syringe filled with the resin composition to 50 kPa to 92 kPa while holding the frozen syringe filled with the resin composition under a reduced pressure environment of 50 kPa to 92 kPa.

[11] The production method of the syringe filled with the resin composition according to [10], in which the temperature of the reduced pressure environment is −80° C. to 0° C.

[12] The production method of the syringe filled with the resin composition according to [10] or [11], in which a time during which the syringe filled with the resin composition is held under the reduced pressure environment is 30 minutes or more.

[13] The production method of the syringe filled with the resin composition according to any one of [10] to [12], in which the filling amount of the resin composition into the syringe barrel is 10% to 95% of the internal capacity of the syringe.

Effects of Invention

According to the present invention, the barrel cap of the frozen syringe filled with the resin composition can be prevented from being detached even when the environment temperature changes during storage or transportation.

BRIEF DESCRIPTION OF DRAWINGS

FIG. 1 is a cross-sectional view illustrating a schematic configuration of a syringe filled with a resin composition according to a first embodiment of the present invention.

DESCRIPTION OF EMBODIMENTS

Hereinafter, a syringe filled with a resin composition, a production method thereof, and a storage method thereof according to embodiments of the present invention will be described based on embodiments. However, the below-described embodiments are examples for embodying the technological idea of the present invention. The present disclosure is not limited to the syringe filled with the resin composition, the production method thereof, and the storage method thereof described below.

A syringe filled with a resin composition according to a first embodiment of the present invention includes a syringe having a syringe barrel, a resin composition filling the syringe barrel, a plunger inserted in the syringe barrel, a barrel cap blocking an opening of the syringe barrel, and a spatial part between the plunger and the barrel cap in the syringe barrel. The pressure of the spatial part in a frozen state is 50 kPa to 92 kPa. As described herein, the "frozen state" refers to a state in which the syringe filled with the resin composition is placed in a temperature environment of 0° C. or lower. The "frozen state" is preferably a state in which the frozen resin composition is solid. Here, a state in which the frozen resin composition is solid refers to a state in which the flowing of the resin composition cannot be visually observed.

FIG. 1 is a cross-sectional view illustrating a schematic configuration of a syringe filled with a resin composition according to a first embodiment of the present invention. In FIG. 1, a syringe 10 filled with a resin composition includes a syringe barrel 1, a resin composition 2 filling the syringe barrel 1, a plunger 3 inserted into the syringe barrel 1, and a barrel cap 5 blocking an opening 4 of the syringe barrel 1. The syringe 10 filled with the resin composition includes a spatial part 6 between the plunger 3 and the barrel cap 5 in the syringe barrel 1. Furthermore, the syringe 10 filled with the resin composition includes a reduced diameter portion 7 at one end of the syringe barrel 1. Preferably, the syringe 10 filled with the resin composition includes a tip cap 8 blocking an opening of the reduced diameter portion 7. The syringe 10 filled with the resin composition may include a flange 9 at the other end opposite the reduced diameter portion 7 of the syringe barrel 1.

The syringe filled with the resin composition according to the first embodiment of the present invention includes the spatial part between the plunger and the barrel cap in the syringe barrel. The pressure of the spatial part in a frozen state is 50 kPa to 92 kPa. The pressure of the spatial part between the plunger and the barrel cap in the syringe barrel of the syringe filled with the resin composition is reduced to lower than 101.3 kPa (1 atm) as the standard atmospheric pressure in a frozen state. Accordingly, for example, the barrel cap can be prevented from being detached, even if the volume of gas present in the spatial part expands due to temperature change when the syringe filled with the resin composition according to the first embodiment of the present invention frozen at 0° C. or lower is thawed to normal temperature (for example, 25° C.) when in use. If the barrel cap can be prevented from being detached, foreign substances can be prevented from being mixed into the syringe. The pressure of the spatial part between the plunger and the barrel cap in the syringe barrel of the syringe filled with the resin composition, in a frozen state, is preferably 50.5 kPa to 90.0 kPa, more preferably 50.5 kPa to 85.0 kPa, and further preferably 50.5 kPa to 82.0 kPa.

The spatial part in the syringe barrel of the syringe filled with the resin composition is reduced in pressure in a frozen state by the later-described production method of the syringe filled with the resin composition. More particularly, in a state in which the resin composition filling the syringe barrel is frozen at 0° C. or lower, the pressure of the spatial part in the syringe barrel is reduced to 50 kPa to 92 kPa. In a state in which the resin composition filling the syringe barrel is frozen, the spatial part between the plunger and the barrel cap in the syringe barrel is reduced in pressure. This can reduce the pressure of the spatial part between the plunger and the barrel cap in the syringe barrel without air mixed in the resin composition filling the syringe barrel during pressure reduction.

The filling amount of the resin composition in the syringe barrel of the syringe filled with the resin composition is preferably 10% to 95% of the internal capacity of the syringe. The internal capacity of the syringe refers to a volume of liquid or gas which can be placed in the syringe barrel. When the filling amount of the resin composition in the syringe barrel of the syringe filled with the resin composition is 10% to 95% of the internal capacity of the syringe, a spatial part is formed between the plunger and the barrel cap in the syringe barrel even when the volume of the plunger is excluded. The filling amount of the resin composition in the syringe barrel of the syringe filled with the resin composition is more preferably 10% to 90% of the internal capacity of the syringe.

It is preferable that a gap cannot be visually observed in the syringe filled with the resin composition. A gap as described here refers to a space present between the inner wall of the syringe and the resin composition. When the pressure of the spatial part is reduced to 50 kPa to 92 kPa while the resin composition in the syringe filled with the resin composition is in a frozen state at 0° C. or lower, the frozen resin composition is in a solid state without fluidity. Therefore, air is unlikely to enter the resin composition during pressure reduction. If there is no visually observable gap in the syringe filled with the resin composition, air is more unlikely to enter the resin composition. Therefore, even if the volume of gas present in the spatial part expands due to temperature change when the resin composition is thawed, the barrel cap can be prevented from being detached. As a result, foreign substances can be prevented from being mixed into the syringe.

The resin composition to fill the syringe preferably contains at least one resin selected from epoxy resin and acrylic resin. The at least one resin selected from epoxy resin and acrylic resin is used as a material for a sealant of mechanical components or electronic components, an adhesive, a paste for forming electrical circuits or electrical circuits, or the like.

The epoxy resin is preferably in a liquid form at normal temperature. However, epoxy resin to be in a solid form at normal temperature may be used. Epoxy resin to be in a solid form at normal temperature can be diluted with liquid epoxy resin, a solvent, or a diluent, thereby to be used as liquid resin. Epoxy resin refers to a resin having in its molecule at least one epoxy or glycidyl group. Examples of the epoxy resin include bisphenol A type epoxy resin, bisphenol F type epoxy resin, derivatives of these epoxy resins (for example, alkylene oxide adducts), hydrogenated bisphenol A type epoxy resin, hydrogenated bisphenol F type epoxy resin, brominated bisphenol A type epoxy resin, biphenyl type epoxy resin, naphthalene type epoxy resin, glycidyl ether type epoxy resin including alkyl glycidyl ether, alkyl phenyl glycidyl ether, alkenyl glycidyl ether, alkynyl glycidyl ether, and phenyl glycidyl ether, each having 6 to 36 carbon atoms, glycidyl ester type epoxy resin including alkyl glycidyl ester, alkenyl glycidyl ester, and phenyl glycidyl ester, each having 6 to 36 carbon atoms, and silicone epoxy resin. One of these epoxy resins may be singly used. Alternatively, two or more epoxy resins may be used in combination.

The acrylic resin is preferably (meth)acrylic resin. Acrylic resin refers to a compound having in its molecule a (meth) acryloyl group. Examples of the (meth)acrylic resin include methyl (meth)acrylate, ethyl (meth)acrylate, n-butyl (meth) acrylate, isobutyl (meth)acrylate, tert-butyl (meth)acrylate, isodecyl (meth)acrylate, lauryl (meth)acrylate, tridecyl (meth)acrylate, cetyl (meth)acrylate, stearyl (meth)acrylate, isoamyl (meth)acrylate, isostearyl (meth)acrylate, behenyl (meth)acrylate, 2-ethylhexyl (meth)acrylate, other alkyl (meth)acrylates, cyclohexyl (meth)acrylate, tert-butyl cyclohexyl (meth)acrylate, tetrahydrofurfuryl (meth)acrylate, benzyl (meth)acrylate, phenoxyethyl (meth)acrylate, isobornyl (meth)acrylate, glycidyl (meth)acrylate, trimethylol propane tri(meth)acrylate, zinc mono(meth)acrylate, zinc di(meth)acrylate, dimethylaminoethyl (meth)acrylate, diethyl aminoethyl (meth)acrylate, neopentyl glycol (meth) acrylate, trifluoroethyl (meth)acrylate, 2,2,3,3-tetrafluoropropyl (meth)acrylate, 2,2,3,3,4,4-hexafluorobutyl (meth) acrylate, perfluorooctyl (meth)acrylate, perfluorooctylethyl (meth)acrylate, ethylene glycol di(meth)acrylate, propylene glycol di(meth)acrylate, 1,4-butanediol di(meth)acrylate, 1,6-hexanediol di(meth)acrylate, 1,9-nonanediol di(meth) acrylate, 1,3-butanediol di(meth)acrylate, 1,10-decanediol di(meth)acrylate, tetramethylene glycol di(meth)acrylate, methoxyethyl (meth)acrylate, butoxyethyl (meth)acrylate, ethoxydiethylene glycol (meth)acrylate, methoxypolyalkylene glycol mono(meth)acrylate, octoxypolyalkylene glycol mono(meth)acrylate, lauroxypolyalkylene glycol mono (meth)acrylate, stearoxypolyalkylene glycol mono(meth) acrylate, allyloxypolyalkylene glycol mono(meth)acrylate, nonylphenoxypolyalkylene glycol mono(meth)acrylate, tricyclodecane dimethanol diacrylate, N-(meth)acryloyloxyethyl maleimide, N-(meth)acryloyloxyethyl hexahydrophthalimide, and N-(meth)acryloyloxyethyl phthalimide. Further examples include (meth)acrylamide including N,N'-methylenebis(meth)acrylamide, N,N'-ethylenebis(meth) acrylamide, and 1,2-di(meth)acrylamide ethylene glycol. One of these acrylic resins may be singly used. Alternatively, two or more acrylic resins may be used in combination.

An example of the acrylic resin is poly(meth)acrylate. Examples of the poly(meth)acrylate includes a copolymer of (meth)acrylic acid and (meth)acrylate and a copolymer of (meth)acrylate having a hydroxyl group and (meth)acrylate having no polar group. Examples of the acrylic resin include (meth)acrylate having a hydroxyl group including 2-hydroxyethyl (meth)acrylate, 2-hydroxypropyl (meth)acrylate, 3-hydroxypropyl (meth)acrylate, 2-hydroxybutyl (meth) acrylate, 3-hydroxybutyl (meth)acrylate, 4-hydroxybutyl (meth)acrylate, 1,2-cyclohexanediol mono(meth)acrylate, 1,3-cyclohexanediol mono(meth)acrylate, 1,4-cyclohexanediol mono(meth)acrylate, 1,2-cyclohexanedimethanol mono (meth)acrylate, 1,3-cyclohexanedimethanol mono(meth) acrylate, 1,4-cyclohexanedimethanol mono(meth)acrylate, 1,2-cyclohexanediethanol mono(meth)acrylate, 1,3-cyclohexanediethanol mono(meth)acrylate, 1,4-cyclohexanediethanol mono(meth)acrylate, glycerin mono(meth)acrylate, glycerin di(meth)acrylate, trimethylolpropane mono(meth) acrylate, trimethylolpropane di(meth)acrylate, pentaerythritol mono(meth)acrylate, pentaerythritol di(meth)acrylate, pentaerythritol tri(meth)acrylate, or neopentyl glycol mono (meth)acrylate, and (meth)acrylate having a carboxy group obtained through a reaction between these (meth)acrylates having a hydroxyl group and dicarboxylic acid or a derivative thereof. Examples of the dicarboxylic acid usable here include oxalic acid, malonic acid, succinic acid, glutaric acid, adipic acid, pimelic acid, suberic acid, azelaic acid, sebacic acid, maleic acid, fumaric acid, phthalic acid, tetrahydrophthalic acid, hexahydrophthalic acid, and derivatives thereof. One of these acrylic resins may be singly used. Alternatively, two or more acrylic resins may be used in combination.

The resin composition filling the syringe may include, other than at least one resin selected from epoxy resin and acrylic resin, at least one additive selected from the group consisting of a filler, a curing agent, a solvent, a reactive diluent, an elastomer, a coupling agent, a flux agent, a defoamer, a surface controlling agent, a rheology controlling agent, a colorant, a plasticizer, and a dispersant.

More specifically, when the viscosity at 25° C. of the resin composition filling the syringe is in a range of not less than 2.5 Pa·s and less than 20 Pa·s, the viscosity can be measured at 50 rpm using, for example, a rotary viscometer RV type (spindle SC-14) (manufactured by Brookfield Co.). Also, when the viscosity at 25° C. of the resin composition filling the syringe is in a range of not less than 20 Pa·s and less than 200 Pa·s, the viscosity can be measured at 50 rpm using, for example, a rotary viscometer HBDV-1 (spindle SC4-14) (manufactured by Brookfield Co.). Also, when the viscosity at 25° C. of the resin composition filling the syringe is in a range of 200 Pa·s or more and 1,000 Pa·s or less, the viscosity can be measured at 10 rpm using, for example, a rotary viscometer HBDV-1 (spindle SC4-14) (manufactured by Brookfield Co.). The viscosity of the resin composition of less than 200 Pa·s obtained through measurement at 25° C. and a rotational speed of 50 rpm and the viscosity of the resin composition of 200 Pa·s or more obtained through measurement at 25° C. and a rotational speed of 10 rpm, using the above-described rotary viscometers, are preferably 2.5 Pa·s to 650 Pa·s. When the viscosities of the resin compositions obtained through measurement under the above-described conditions using the above-described rotary viscometers are 0.4 Pa·s to 650 Pa·s, large voids are unlikely to be mixed into the resin composition when filling the syringe with the resin composition. Therefore, air is further unlikely to enter the resin composition when the pressure is reduced in a frozen state. As a result, even when the resin composition is thawed, air is unlikely to be mixed into the resin composition. The viscosities of the resin compositions obtained through measurement under the above-described conditions using the above-described rotary viscometers are more preferably 3 Pa·s to 640 Pa·s and further preferably 5 Pa·s to 630 Pa·s.

Thixotropic indices TI1 to TI3 of the resin composition filling the syringe, measured under the following conditions (1) to (3) are preferably 0.4 to 4.0.
(1) Thixotropic index TI1 that is a ratio between a viscosity at 5 rpm and a viscosity at 50 rpm, when a viscosity measured at 25° C. and 50 rpm using a rotary viscometer (for example, RV type (spindle SC-14), manufactured by Brookfield Co.) is in a range of not less than 2.5 Pa·s and less than 20 Pa·s.
(2) Thixotropic index TI2 that is a ratio between a viscosity at 5 rpm and a viscosity at 50 rpm, when a viscosity measured at 25° C. and 50 rpm using a rotary viscometer (for example, rotary viscometer HBDV-1 (spindle SC4-14), manufactured by Brookfield Co.) is in a range of not less than 20 Pa·s and less than 200 Pa·s.
(3) Thixotropic index TI3 that is a ratio between a viscosity at 1 rpm and a viscosity at 10 rpm, when a viscosity measured at 25° C. and 10 rpm using a rotary viscometer (for example, rotary viscometer HBDV-1 (spindle SC4-14), manufactured by Brookfield Co.) is in a range of 200 Pa·s or more and 1,000 Pa·s or less.

Thixotropic index TI1 measured under the above-described condition (1) is a ratio between viscosity $V1_{5\ rpm}$ at 5 rpm and viscosity $V1_{50\ rpm}$ at 50 rpm, measured at 25° C. using a rotary viscometer RV type (spindle SC-14) (manufactured by Brookfield Co.). Thixotropic index TI1 is calculated according to equation (II) below.

[Mathematical Formula 1]

$$TI1 = V1_{5\ rpm}/V1_{50\ rpm} \quad (II)$$

Thixotropic index TI2 measured under the above-described condition (2) is a ratio between viscosity $V2_{5\ rpm}$ at 5 rpm and viscosity $V2_{50\ rpm}$ at 50 rpm, measured at 25° C. using a rotary viscometer HBDV-1 (spindle SC4-14) (manufactured by Brookfield Co.). Thixotropic index TI2 is calculated according to equation (III) below.

[Mathematical Formula 2]

$$TI2 = V2_{5\ rpm}/V2_{50\ rpm} \quad (III)$$

Thixotropic index TI3 measured under the above-described condition (3) is a ratio between viscosity $V3_{1\ rpm}$ at 1 rpm and viscosity $V3_{10\ rpm}$ at 10 rpm, measured at 25° C. using a rotary viscometer HBDV-1 (spindle SC4-14) (manufactured by Brookfield Co.), and calculated according to Equation (IV) below.

[Mathematical Formula 3]

$$TI3 = V3_{1\ rpm}/V3_{10\ rpm} \quad (IV)$$

Thixotropic indices TI1 to TI3 measured under the measurement condition corresponding to the viscosity of the resin composition are also termed TI values. The TI value is an index representing thixotropic properties, for measuring dependence between shear rate (rotational speed of a viscometer) and viscosity. For a Newtonian fluid, such as water, of which viscosity does not change even when the shear rate changes, the TI value is 1. When the TI value is less than 1, it means that the viscosity is smaller when the shear force is small than when the shear force is large. When the TI value is more than 1, it means that the viscosity is larger when the shear force is small than when the shear force is large. A larger TI value indicates higher thixotropic properties.

In the resin composition filling the syringe, thixotropic indices TI1 to TI3 are preferably in a range of 0.4 to 4.0, when the viscosity measured at 25° C. and 50 rpm is as low as less than 200 Pa·s, or when the viscosity measured at 25° C. and 10 rpm is as high as 200 Pa·s or more and 1,000 Pa·s or less. When the thixotropic indices TI1 to TI3 of the resin composition filling the syringe are 0.4 to 4.0, the dispersibility of small voids mixed in the resin composition improves. Therefore, workability when discharging the resin composition from the syringe improves. The resin composition filling the syringe may have thixotropic properties that are close to for a Newtonian fluid having a thixotropic index of 0.8 to 1.2. Alternatively, the resin composition may have thixotropic properties that are for a non-Newtonian fluid having a thixotropic index of more than 1.2.

An example of the syringe includes a syringe made from polypropylene, polyethylene, polystyrene, or polyester. The volume change of the syringe due to temperature change is preferably small, such that the volume expansion of gas present in the spatial part due to temperature change can be controlled by previously reducing the pressure of the spatial part. Since the volume change due to temperature change is relatively small, the barrel cap can be prevented from being detached. Also, since the cost is relatively low, the syringe is preferably made from polypropylene or polyethylene.

The internal capacity of the syringe is preferably 1 cm$^3$ to 600 cm$^3$. The internal capacity of the syringe is more preferably 3 cm$^3$ to 500 cm$^3$ and further preferably 3 cm$^3$ to 360 cm$^3$. When the internal capacity of the syringe is 1 cm$^3$ to 600 cm$^3$, a spatial part can be provided which can suppress the detachment of the barrel cap even when the volume of the spatial part expands due to temperature change, by previously reducing the pressure of the spatial part between the plunger and the barrel cap in the syringe barrel in a frozen state to 50 kPa to 92 kPa. The internal capacity of the syringe refers to, as described above, a volume of liquid or gas which can be placed in the syringe barrel. Examples of the internal capacity of the syringe include 1 cm$^3$, 2 cm$^3$, 3 cm$^3$, 5 cm$^3$, 10 cm$^3$, 30 cm$^3$, 55 cm$^3$, 180 cm$^3$, 360 cm$^3$, and 600 cm$^3$.

A material constituting the plunger is not particularly limited. Examples of the material constituting the plunger include thermoplastic elastomers including various rubber materials such as natural rubber, butyl rubber, isoprene rubber, butadiene rubber, styrene-butadiene rubber, and silicone rubber and elastic materials such as polyethylene, polyurethane, polyester, and polyamide. Regarding the form of the plunger, at least one end of the plunger may be conical. Alternatively, at least one end of the plunger may be flat. The volume of the plunger is usually 0.3% to 10.0% of the internal capacity of the syringe.

In the syringe filled with the resin composition according to the first embodiment of the present invention, the spatial part between the plunger and the barrel cap in the syringe barrel is previously reduced in pressure to a specific pressure in a frozen state. Therefore, for example, when the syringe is stored at 0° C. or lower and thawed to normal temperature (for example, 25° C.) when in use, the barrel cap can be prevented from being detached even if the volume of gas present in the spatial part expands due to temperature change. The syringe filled with the resin composition according to the first embodiment of the present invention is preferably a syringe for freezing, which is to be frozen and then stored or transported. When used for freezing, the syringe filled with the resin composition is preferably frozen at −80° C. to 0° C. The freezing temperature is more preferably −80° C. to −10° C., further preferably −80° C. to −20° C., and still further preferably −80° C. to −40° C.

Storage Method of Syringe Filled with Resin Composition

A storage method of a syringe filled with a resin composition according to a second embodiment of the present invention is a method of storing a syringe filled with a resin composition at a temperature of −80° C. to 0° C. The freezing and storing at −80° C. to 0° C. as the storage method of the syringe filled with the resin composition suppresses the reaction of the resin composition filling the syringe. This enables the resin composition to be stored in a stable state. The storage temperature of the syringe filled with the resin composition is more preferably −80° C. to −10° C., further preferably −80° C. to −20° C., and still further preferably −80° C. to −40° C. In the storage method of the syringe filled with the resin composition according to the second embodiment of the present invention, the detachment of the barrel cap during thawing can be prevented even after the syringe has been stored at a low temperature of −80° C. to 0° C.

Production Method of Syringe Filled with Resin Composition

A production method of a syringe filled with a resin composition according to a third embodiment of the present invention includes: a step of preparing a syringe filled with a resin composition having a spatial part between a plunger and a barrel cap in a syringe barrel, by filling with a resin composition a syringe barrel having a plunger inserted therein and blocking an opening of the syringe barrel with a barrel cap; a step of freezing the syringe filled with the resin composition at a temperature of −80° C. to 0° C.; and a step of reducing the pressure of the spatial part of the frozen syringe filled with the resin composition to 50 kPa to 92 kPa while holding the frozen syringe filled with the resin composition under a reduced pressure environment of 50 kPa to 92 kPa.

Preparing Step

An example of the method for filling the syringe barrel with the resin composition is a method of filling the syringe with the resin composition through pressurization at a pressure of 0.1 MPa to 0.6 MPa. After the syringe barrel has been filled with the resin composition, a plunger is inserted into the syringe so as to intimately contact the resin composition filling the syringe barrel. Thereafter, the opening of the syringe barrel is blocked with a barrel cap. A tip cap may be fitted to a diameter-reduced opening of the syringe filled with the resin composition.

The filling amount of the resin composition into the syringe barrel is preferably 10% to 95% of the internal capacity of the syringe. When the filling amount of the resin composition into the syringe is 10% to 95% of the internal capacity of the syringe, the barrel cap can be prevented from being detached even when the volume of the spatial part expands due to temperature change, by reducing the pressure of the spatial part excluding the volume of the plunger in a frozen state to 50 kPa to 92 kPa. The filling amount of the resin composition into the syringe barrel is more preferably 10% to 90% of the internal capacity of the syringe.

Freezing Step

The prepared syringe filled with the resin composition is frozen at a temperature of −80° C. to 0° C. The freezing temperature is more preferably −80° C. to −10° C., further preferably −80° C. to −20° C., and still further preferably −80° C. to −40° C. The freezing time is not particularly limited, as long as it is a time taken for the resin composition in the syringe barrel to lose fluidity due to freezing and become solid.

Pressure Reducing Step

The frozen syringe filled with the resin composition is held in a frozen state under a reduced pressure environment at 50 kPa to 92 kPa. Then, the pressure of the spatial part of the frozen syringe filled with the resin composition is reduced in a frozen state to 50 kPa to 92 kPa. The temperature of the reduced pressure environment is preferably 0° C. or lower, more preferably −80° C. to 0° C., further preferably −80° C. to −20° C., and still further preferably −80° C. to −40° C. For preventing the detachment of the barrel cap, the pressure of the reduced pressure environment in a frozen state is preferably 50.5 kPa to 90.0 kPa, more preferably 50.5 kPa to 85.0 kPa, and further preferably 50.5 kPa to 82.0 kPa.

A time during which the syringe filled with the resin composition is held under the reduced pressure environment is preferably 30 minutes or more, more preferably 1 hour or more, and further preferably 3 hours or more. Also, the holding time is preferably 15 hours or less and more preferably 12 hours or less. When a time during which the syringe filled with the resin composition is held under the reduced pressure environment is 30 minutes or more and 15 hours or less, the spatial part between the plunger and the barrel cap in the syringe barrel of the syringe filled with the resin composition can be reduced in pressure to a specific pressure. When a time during which the syringe filled with the resin composition is held under the reduced pressure environment is less than 30 minutes, the spatial part between the plunger and the barrel cap in the syringe barrel cannot be reduced in pressure to a specific pressure in some cases. Also, even when held for a long time, more than 15 hours, under the reduced pressure environment, the pressure cannot be reduced to a pressure smaller than the pressure under the reduced pressure environment.

In the freezing step and the pressure reducing step, an apparatus capable of performing both freezing and pressure reducing is preferably used. As a preferable example, the syringe filled with the resin composition disposed in a chamber is frozen at −80° C. to 0° C. Thereafter, the pressure in the chamber is reduced in a frozen state to 50 kPa to 92 kPa, by a vacuum pump connected to the chamber. Then, the pressure of the spatial part between the plunger and the barrel cap, in the syringe barrel of the syringe filled with the resin composition disposed in the chamber, is reduced to 50 kPa to 92 kPa. The syringe filled with the resin composition may be reduced in pressure to 50 kPa to 92 kPa in a continued frozen state at a temperature of −80° C. to 0° C. The chamber capable of performing both freezing and pressure reducing preferably includes a cooler capable of freezing to −80° C. to 0° C., a vacuum pump capable of reducing the pressure of the inside with the chamber sealed, a pressure gauge capable of measuring the pressure in the chamber, and a leak valve for, after pressure reduction, restoring the pressure in the chamber to the standard atmospheric pressure.

In the syringe filled with the resin composition produced by the production method according to the present disclosure, the pressure of the spatial part between the plunger and the barrel cap in the syringe barrel is reduced to 50 kPa to 92 kPa. Therefore, for example, when the syringe is stored at 0° C. or lower and thawed to normal temperature (for example, 25° C.), the barrel cap can be prevented from being detached even if the volume of gas present in the spatial part expands due to temperature change. As a result, foreign substances can be prevented from being mixed into the syringe.

EXAMPLES

Hereinafter, the present invention will be more specifically described with reference to examples. The present invention is not limited to these examples.

Resin compositions Epo1 to Epo7 and ACR1 used in Examples and Comparative Examples were produced so as to have formulation ratios indicated in Table 1. The resin compositions were prepared by kneading the following raw materials using a triple roll mill. It is noted that the numerical values regarding each makeup in Table are illustrated in parts by mass.
A: bisphenol F type epoxy resin, product name YDF8170, manufactured by Nippon Steel Chemical Co., Ltd., epoxy equivalent 158 g/eq.
B: amine curing agent: 4,4'-diamino-3,3'-diethyldiphenylmethane, product name Kayahard A-A (HDAA), manufactured by Nippon Kayaku Co., Ltd.
C: tricyclodecane dimethanol diacrylate, product name A-DCP, manufactured by Shin-Nakamura Kogyo Co., Ltd.
D: polymerization initiator, t-butyl-α-cumyl peroxide, product name Perbutyl C, manufactured by Nof Corporation.
E-1: inorganic filler, highly pure synthetic spherical silica (silane coupling agent (3-glycidoxypropyltrimethoxysilane) surface treatment silica filler) (average particle size 0.6 μm), product name SE2200-SEE, manufactured by Admatechs Company Limited.
E-2: inorganic filler, hydrophobic fumed silica (average particle size 20 nm), product name R805, manufactured by Nippon Aerosil Co., Ltd.

(manufactured by Brookfield Co.). Thixotropic index TI1 was measured according to equation (II) described above.

(2) When the viscosity at 25° C. is in a range of not less than 20 Pa·s and less than 200 Pa·s, the viscosity was measured at 50 rpm using a rotary viscometer HBDV-1 (spindle SC4-14) (manufactured by Brookfield Co.). Thixotropic index TI2 was measured according to equation (III) described above.

(3) When the viscosity at 25° C. is in a range of 200 Pa·s or more and 1,000 Pa·s or less, the viscosity was measured at 10 rpm using a rotary viscometer HBDV-1 (spindle SC4-14) (manufactured by Brookfield Co.). Thixotropic index TI3 was measured according to equation (IV) described above.

Types of syringes used in Examples and Comparative Examples are illustrated below. The material and capacity of the syringe as well as the material of the plunger are illustrated in Table 2.

(1) size: 5 cm³, material: polypropylene (PP), manufactured by Nordson EFD LLC., product name: Optimum (registered trademark), S1 is illustrated as a type of the syringe in Table.

(2) size: 10 cm³, material: polypropylene (PP), manufactured by Nordson EFD LLC., product name: Optimum (registered trademark), S2 is illustrated as a type of the syringe in Table.

(3) size: 10 cm³, material: polypropylene (PP), manufactured by Musashi Engineering, Inc., product name: PSY-10E, S3 is illustrated as a type of the syringe in Table.

(4) size: 10 cm³, material: polypropylene (PP), manufactured by Iwashita Engineering, Inc., product name: P510S, S4 is illustrated as a type of the syringe in Table.

(5) size: 10 cm³, material: polypropylene (PP), San-Ei Tech Ltd., product name: SH11LL-B, S5 is illustrated as a type of the syringe in Table.

(6) size: 30 cm³, material: polypropylene (PP), manufactured by Nordson EFD LLC., product name: Optimum (registered trademark), S6 is illustrated as a type of the syringe in Table.

TABLE 1

|   |   | Epo1 | Epo2 | Epo3 | Epo4 | Epo5 | Epo6 | Epo7 | ACR1 |
|---|---|---|---|---|---|---|---|---|---|
| A | Bisphenol F type epoxy resin | 100.0 | 100.0 | 100.0 | 100.0 | 100.0 | 100.0 | 100.0 | — |
| B | 4,4'-diamino-3,3'-diethyldiphenylmethane | 40.8 | 40.8 | 40.8 | 40.8 | 40.8 | 40.8 | 40.8 | — |
| C | Tricyclodecane dimethanol diacrylate | — | — | — | — | — | — | — | 100.00 |
| D | tbutyl-α-cumylperoxide | — | — | — | — | — | — | — | 0.20 |
| E-1 | Highly pure synthetic spherical silica (average particle size 0.6 μm) | 102.0 | 140.8 | 194.5 | 299.3 | 1253.5 | 1584.5 | — | 158.0 |
| E-2 | Hydrophobic fumed silica (average particle size 20 nm) | — | — | — | — | 14.1 | 35.2 | — | 5.3 |
| Viscosity (Pa · s) | | 5 | 10 | 15 | 60 | 400 | 623 | 0.5 | 15 |
| TI value | | 1 | 0.9 | 1 | 0.9 | 1.5 | 3.1 | 0.9 | 3 |

For the produced resin compositions, the viscosity (Pa·s) and the thixotropic index were measured under the following conditions. The results are indicated in Table 1. It is noted that in Tables 1 and 3 to 5, TI1 to TI3 measured under the condition corresponding to the viscosity of the resin composition are described as TI values.

(1) When the viscosity at 25° C. is in a range of not less than 2.5 Pa·s and less than 20 Pa·s, the viscosity was measured at 50 rpm using a rotary viscometer RV type (spindle SC-14)

(7) size: 55 cm³, material: polypropylene (PP), manufactured by Nordson EFD LLC., product name: Optimum (registered trademark), S7 is illustrated as a type of the syringe in Table.

(8) size: 180 cm³ (6 ounce, 6 oz), material: polyethylene (PE), manufactured by Nordson EFD LLC., product name: Optimum (registered trademark), S8 is illustrated as a type of the syringe in Table.

(9) size: 360 cm³ (12 ounce, 12 oz), material: polyethylene (PE), manufactured by Nordson EFD LLC., product name: Optimum (registered trademark), S9 is illustrated as a type of the syringe in Table.

(10) size: 355 cm³ (12 oz), material: polypropylene (PP), manufactured by SEMCO Inc., product name: SEMCO 120 ounce cartridge, S10 is illustrated as a type of the syringe in Table.

TABLE 2

|  | Syringe |  | Plunger |
| --- | --- | --- | --- |
| S1 | 5 cm³ | PP | PE |
| S2 | 10 cm³ | PP | PE |
| S3 | 10 cm³ | PP | PE |
| S4 | 10 cm³ | PP | PE |
| S5 | 10 cm³ | PP | PE |
| S6 | 30 cm³ | PP | PE |
| S7 | 55 cm³ | PP | PE |
| S8 | 180 cm³ (6 oz) | PE | PE |
| S9 | 360 cm³ (12 oz) | PE | PE |
| S10 | 355 cm³ (12 oz) | PP | PE |

Example 1

The resin indicated in Table 1 was mixed and dispersed using a triple roll mill. Thereafter, the viscosity and thixotropic index (TI) value of the resin composition before filling the syringe were measured by the above-described method. The result is indicated in Table 3. With this resin composition in the amount indicated in Table 3, the syringe barrel of the syringe having the material and capacity indicated in Table 3 was filled through pressurization at a pressure of 0.1 to 0.6 MPa. A plunger was inserted into the syringe so as to contact the resin composition filling the syringe barrel. Then, the opening of the syringe barrel was blocked with a barrel cap. In this manner, a spatial part was formed between the plunger and the barrel cap in the syringe barrel. Accordingly, a syringe filled with a resin composition was produced. To a diameter-reduced opening at one end of the syringe, a tip cap was fitted. Thereafter, the syringe filled with the resin composition was frozen and stored at the temperature and for the time indicated in Table 3, using a freezer (SANYO Co., trade name MDF-394AT-PJ). Thereafter, while the temperature indicated in Table 3 was kept, the environment in the chamber of the freezer was reduced in pressure by a vacuum pump (manufactured by Shinko Seiki Co., Ltd., trade name SVC-300). During the pressure reduction, the syringe filled with the resin composition in the chamber was held at the temperature and pressure for the time indicated in Table 3 using a regulator. In this manner, the pressure of the spatial part between the plunger and the barrel cap of the syringe filled with the resin composition became the same as the pressure of the reduced pressure environment. Thereafter, the syringe filled with the resin composition removed from the chamber was left to stand at room temperature (about 25° C.) for 1 hour. In this manner, the resin composition in the syringe barrel was thawed. As test samples, 15 samples were prepared under the same condition. Then, whether the barrel cap was spontaneously detached was visually observed during freezing and storing, during pressure reduction, or during thawing. When the barrel cap was detached, the number of detached barrel caps with respect to 15 test samples was measured. The result is indicated in Table 3. Also, whether a gap can be observed in the resin composition in the syringe barrel after thawed was visually observed. When a gap is generated, a gap can be observed between the plunger and the resin composition.

Examples 2 to 3

For each Example, 15 syringes filled with a resin composition for a test sample were prepared in a similar manner to Example 1, except that the pressure during pressure reduction in a frozen state was changed as indicated in Table 3. The detachment of the barrel cap and the presence or absence of a gap under each condition were observed in a similar manner to Example 1.

Examples 4 to 5

For each Example, 15 syringes filled with a resin composition for a test sample were prepared in a similar manner to Example 1, except that the freezing temperature of the syringe filled with the resin composition was changed as indicated in Table 3. The detachment of the barrel cap and the presence or absence of a gap under each condition were observed in a similar manner to Example 1.

Examples 6 to 7

For each Example, 15 syringes filled with a resin composition for a test sample were prepared in a similar manner to Example 1, except that the filling amount of the resin composition in the syringe barrel was changed as indicated in Table 3. The detachment of the barrel cap and the presence or absence of a gap under each condition were observed in a similar manner to Example 1.

Comparative Example 1

Fifteen syringes filled with a resin composition for a test sample were prepared in a similar manner to Example 1, except that the pressure of the spatial part between the plunger and the barrel cap of the syringe filled with the resin composition in a frozen state, placed in a chamber at the standard atmospheric pressure (101.3 kPa), became the same as the pressure of the reduced pressure environment. The detachment of the barrel cap and the presence or absence of a gap under each condition were measured in a similar manner to Example 1.

Comparative Example 2

Fifteen syringes filled with a resin composition for a test sample were prepared in a similar manner to Example 1, except that the pressure of the spatial part between the plunger and the barrel cap of the syringe filled with the resin composition in a frozen state, placed in a chamber at 40.5 kPa, became the same as the pressure of the reduced pressure environment. The detachment of the barrel cap and the presence or absence of a gap under each condition were observed in a similar manner to Example 1.

Reference Example 3

Fifteen syringes filled with a resin composition for a test sample were prepared in a similar manner to Example 1, except that the syringe filled with the resin composition was reduced in pressure under an environment at 25° C. without being frozen. The detachment of the barrel cap and the presence or absence of a gap under each condition were observed in a similar manner to Example 1.

TABLE 3

|  |  | Example 1 | Example 2 | Example 3 | Example 4 | Example 5 | Example 6 | Example 7 | Comparative Example 1 | Comparative Example 2 | Reference Example 3 |
|---|---|---|---|---|---|---|---|---|---|---|---|
| Syringe | Internal capacity (cm$^3$) | 30 | 30 | 30 | 30 | 30 | 30 | 30 | 30 | 30 | 30 |
|  | Material | PP | PP | PP | PP | PP | PP | PP | PP | PP | PP |
|  | Type | S6 | S6 | S6 | S6 | S6 | S6 | S6 | S6 | S6 | S6 |
| Plunger | Material | PE | PE | PE | PE | PE | PE | PE | PE | PE | PE |
| Resin composition | Filling amount (cm$^3$) | 20 | 20 | 20 | 20 | 20 | 10 | 30 | 20 | 20 | 20 |
|  | Viscosity (Pa·s) | 15 | 15 | 15 | 15 | 15 | 15 | 15 | 15 | 15 | 15 |
|  | TI value | 1.0 | 1.0 | 1.0 | 1.0 | 1.0 | 1.0 | 1.0 | 1.0 | 1.0 | 1.0 |
|  | Type of resin | EPO3 | EPO3 | EPO3 | EPO3 | EPO3 | EPO3 | EPO3 | EPO3 | EPO3 | EPO3 |
| Freezing condition | Temperature (° C.) | −40 | −40 | −40 | −20 | −60 | −40 | −40 | −40 | −40 | 25 |
|  | Storage time (hr) | 8 | 8 | 8 | 8 | 8 | 8 | 8 | 8 | 8 | 0 |
| Pressure condition | Pressure (kPa) | 81.1 | 50.7 | 91.2 | 81.1 | 81.1 | 81.1 | 81.1 | 101.3 | 40.5 | 81.1 |
|  | Holding time (hr) | 6 | 6 | 6 | 6 | 6 | 6 | 6 | 6 | 6 | 6 |
| Number of barrel caps detached during pressure reduction |  | 0 | 0 | 0 | 0 | 0 | 0 | 0 | 0 | 13 | 0 |
| Gap | Presence or absence | Absence | Absence | Absence | Absence | Absence | Absence | Absence | Absence | Absence | Presence |
| Number of barrel caps detached during thawing |  | 0 | 0 | 0 | 0 | 0 | 0 | 0 | 6 | 0 | Not applicable |

As indicated in Table 3, in the syringe filled with the resin composition according to each of Examples 1 to 3, the barrel cap was not detached during pressure reduction and during thawing, even when the pressure of the spatial part in a frozen state was changed to a range of 50 kPa to 92 kPa. A gap was not observed between the inner wall of the syringe barrel and the resin composition. Also, in the syringe filled with the resin composition according to each of Examples 4 and 5, the barrel cap was not detached during pressure reduction and during thawing, even when the temperature in a frozen state was changed to a temperature of 0° C. or lower. A gap was not observed between the inner wall of the syringe barrel and the resin composition. Also, in the syringe filled with the resin composition according to each of Examples 6 and 7, the barrel cap was not detached during pressure reduction and during thawing, even when the filling amount of the resin composition into the syringe barrel was changed. A gap was not observed between the inner wall of the syringe barrel and the resin composition.

As indicated in Table 3, in the syringe filled with the resin composition according to Comparative Example 1, the pressure of the spatial part in a frozen state was the same as the standard atmospheric pressure, 101.3 kPa. Therefore, when the resin composition was thawed, gas present in the spatial part expanded with temperature change. Therefore, the barrel cap was detached. In the syringe filled with the resin composition according to Comparative Example 2, the pressure of the spatial part in a frozen state is 40.5 kPa, which is excessively low. Therefore, the barrel cap was detached during pressure reduction. The syringe filled with the resin composition according to Reference Example 3 is reduced in pressure at normal temperature (25° C.). Therefore, air was mixed in during pressure reduction. Therefore, a gap was observed between the inner wall of the syringe barrel and the resin composition.

Examples 8 to 13

In each of Examples 8 to 13, 15 syringes filled with a resin composition for a test sample were prepared in a similar manner to Example 1, except that the resin composition having the viscosity and the TI value indicated in Table 4 was used. The detachment of the barrel cap and the presence or absence of a gap under each condition were observed in a similar manner to Example 1.

Example 14

In Example 14, 15 syringes filled with a resin composition for a test sample were prepared in a similar manner to Example 1, except that the resin composition having the TI value indicated in Table 4 was used. The detachment of the barrel cap and the presence or absence of a gap under each condition were observed in a similar manner to Example 1.

TABLE 4

|  |  | Example 8 | Example 9 | Example 10 | Example 11 | Example 12 | Example 13 | Example 14 |
|---|---|---|---|---|---|---|---|---|
| Syringe | Internal capacity (cm$^3$) | 30 | 30 | 30 | 30 | 30 | 30 | 30 |
|  | Material | PP | PP | PP | PP | PP | PP | PP |
|  | Type | S6 | S6 | S6 | S6 | S6 | S6 | S6 |
| Plunger | Material | PE | PE | PE | PE | PE | PE | PE |
| Resin composition | Filling amount (cm$^3$) | 20 | 20 | 20 | 20 | 20 | 20 | 20 |
|  | Viscosity (Pa·s) | 5 | 10 | 0.5 | 60 | 400 | 623 | 15 |
|  | TI value | 1.0 | 0.9 | 0.9 | 0.9 | 1.5 | 3.1 | 3.0 |
|  | Type of resin | EPO1 | EPO2 | EPO7 | EPO4 | EPO5 | EPO6 | ACR1 |
| Freezing condition | Temperature (° C.) | −40 | −40 | −40 | −40 | −40 | −40 | −40 |
|  | Storage time (hr) | 8 | 8 | 8 | 8 | 8 | 8 | 8 |

TABLE 4-continued

|  |  | Example 8 | Example 9 | Example 10 | Example 11 | Example 12 | Example 13 | Example 14 |
|---|---|---|---|---|---|---|---|---|
| Pressure condition | Pressure (kPa) | 81.1 | 81.1 | 81.1 | 81.1 | 81.1 | 81.1 | 81.1 |
|  | Holding time (hr) | 6 | 6 | 6 | 6 | 6 | 6 | 6 |
| Number of barrel caps detached during pressure reduction |  | 0 | 0 | 0 | 0 | 0 | 0 | 0 |
| Gap | Presence or absence | Absence | Absence | Absence | Absence | Absence | Absence | Absence |
| Number of barrel caps detached during thawing |  | 0 | 0 | 0 | 0 | 0 | 0 | 0 |

As indicated in Table 4, in the syringe filled with the resin composition according to each of Examples 8 to 13 and Example 14, the barrel cap was not detached during pressure reduction and during thawing, even when the viscosity and the TI value of the resin composition filling the syringe barrel were changed or even when the type of resin was changed. A gap was not observed between the inner wall of the syringe barrel and the resin composition.

Examples 15 to 23

In each of Examples 15 to 23, 15 syringes filled with a resin composition for a test sample were prepared in a similar manner to Example 1, except that the types of the syringe and the resin composition as well as the filling amount thereof were changed as indicated in Table 5. The detachment of the barrel cap and the presence or absence of a gap under each condition were observed in a similar manner to Example 1.

TABLE 5

|  |  | Example 15 | Example 16 | Example 17 | Example 18 | Example 19 | Example 20 | Example 21 | Example 22 | Example 23 |
|---|---|---|---|---|---|---|---|---|---|---|
| Syringe | Internal capacity (cm$^3$) | 5 | 55 | 180 | 360 | 355 | 10 | 10 | 10 | 10 |
|  | Material | PP | PP | PE | PE | PP | PP | PP | PP | PP |
|  | Type | S1 | S7 | S8 | S9 | S10 | S2 | S3 | S4 | S5 |
| Plunger | Material | PE | PE | PE | PE | PE | PE | PE | PE | PE |
| Resin composition | Filling amount (cm$^3$) | 3 | 30 | 160 | 300 | 300 | 10 | 10 | 10 | 10 |
|  | Viscosity (Pa·s) | 15 | 15 | 15 | 15 | 15 | 15 | 15 | 15 | 15 |
|  | TI value | 1.0 | 1.0 | 1.0 | 1.0 | 1.0 | 1.0 | 1.0 | 1.0 | 1.0 |
|  | Type of resin | EPO3 | EPO3 | EPO3 | EPO3 | EPO3 | EPO3 | EPO3 | EPO3 | EPO3 |
| Freezing condition | Temperature (° C.) | −40 | −40 | −40 | −40 | −40 | −40 | −40 | −40 | −40 |
|  | Storage time (hr) | 8 | 8 | 8 | 8 | 8 | 8 | 8 | 8 | 8 |
| Pressure condition | Pressure (kPa) | 81.1 | 81.1 | 81.1 | 81.1 | 81.1 | 81.1 | 81.1 | 81.1 | 81.1 |
|  | Holding time (hr) | 6 | 6 | 6 | 6 | 6 | 6 | 6 | 6 | 6 |
| Number of barrel caps detached during pressure reduction |  | 0 | 0 | 0 | 0 | 0 | 0 | 0 | 0 | 0 |
| Gap | Presence or absence | Absence | Absence | Absence | Absence | Absence | Absence | Absence | Absence | Absence |
| Number of barrel caps detached during thawing |  | 0 | 0 | 0 | 0 | 0 | 0 | 0 | 0 | 0 |

As indicated in Table 5, in the syringe filled with the resin composition according to each of Examples 15 to 23, the barrel cap was not detached during pressure reduction and during thawing, even when the type of the syringe or the amount of the resin composition filling the syringe barrel were changed. A gap was not observed between the inner wall of the syringe barrel and the resin composition.

INDUSTRIAL APPLICABILITY

In the syringe filled with the resin composition according to each of the embodiments of the present invention, the barrel cap can be prevented from being detached due to temperature change during storage or during transportation. Therefore, this syringe can be suitably used as a syringe filled with a viscous material such as a sealant for mechanical components or electronic components, an adhesive, a paste for forming electrical and electronic circuits, or a solder for mounting electronic components.

LIST OF REFERENCE SIGNS

1: syringe barrel, 2: resin composition, 3: plunger, 4: opening of syringe barrel, 5: barrel cap, 6: spatial part, 7: reduced diameter portion, 8: tip cap, 9: flange, 10: syringe filled with resin composition

The invention claimed is:
1. A syringe filled with a resin composition, comprising:
the syringe having a syringe barrel;
the resin composition filling the syringe barrel;
a plunger inserted into the syringe barrel;
a barrel cap blocking an opening of the syringe barrel; and
a spatial part between the plunger and the barrel cap in the syringe barrel,
wherein a pressure of the spatial part in a frozen state is 50 kPa to 92 kPa; and
a viscosity of the resin composition of less than 200 Pa·s measured at 25° C. and a rotational speed of 50 rpm and the viscosity of the resin composition of 200 Pa·s or more measured at 25° C. and a rotational speed of 10 rpm, using a rotary viscometer, are in a range of 2.5 Pa·s to 650 Pa·s.
2. The syringe filled with the resin composition according to claim 1,
wherein a filling amount of the resin composition is 10% to 95% of an internal capacity of the syringe.
3. The syringe filled with the resin composition according to claim 1,
wherein the resin composition contains at least one resin selected from epoxy resin and acrylic resin.

4. The syringe filled with the resin composition according to claim 1,
wherein thixotropic indices TI1 to TI3 of the resin composition measured under any of conditions (1) to (3) below are in a range of 0.4 to 4.0,
(1) Thixotropic index TI1 is a ratio between a viscosity at 5 rpm and the viscosity at 50 rpm, when the viscosity measured at 25° C. and 50 rpm using a rotary viscometer is in a range of not less than 2.5 Pa·s and less than 20 Pa·s,
(2) Thixotropic index TI2 is a ratio between the viscosity at 5 rpm and the viscosity at 50 rpm, when the viscosity measured at 25° C. and 50 rpm using a rotary viscometer is in a range of not less than 20 Pa·s and less than 200 Pa·s, and
(3) Thixotropic index TI3 is a ratio between the viscosity at 1 rpm and the viscosity at 10 rpm, when the viscosity measured at 25° C. and 10 rpm using a rotary viscometer is in a range of 200 Pa·s or more and 1,000 Pa·s or less.

5. The syringe filled with the resin composition according to claim 1,
wherein the syringe is made from polypropylene or polyethylene.

6. The syringe filled with the resin composition according to claim 1,
wherein the syringe has an internal capacity of 1 cm$^3$ to 600 cm$^3$.

7. The syringe filled with the resin composition according to claim 1, which is used for freezing.

8. A storage method of the syringe filled with the resin composition, comprising storing the syringe filled with the resin composition according to claim 1 at a temperature of −80° C. to 0° C.

9. A production method of a syringe filled with a resin composition, comprising:
a step of preparing the syringe filled with the resin composition having a spatial part between a plunger and a barrel cap in a syringe barrel, by filling the syringe barrel having the plunger inserted therein with the resin composition and blocking an opening of the syringe barrel with the barrel cap;
a step of freezing the syringe filled with the resin composition at a temperature of −80° C. to 0° C.; and
a step of reducing a pressure of the spatial part of the frozen syringe filled with the resin composition to 50 kPa to 92 kPa while holding the frozen syringe filled with the resin composition under a reduced pressure environment of 50 kPa to 92 kPa,
wherein a viscosity of the resin composition of less than 200 Pa·s measured at 25° C. and a rotational speed of 50 rpm and the viscosity of the resin composition of 200 Pa·s or more measured at 25° C. and a rotational speed of 10 rpm, using a rotary viscometer, are in a range of 2.5 Pa·s to 650 Pa·s.

10. The production method of the syringe filled with the resin composition according to claim 9,
wherein the step of reducing the pressure of the spatial part of the frozen syringe comprises reducing the pressure of the spatial part of the frozen syringe in a state where the syringe is frozen at the temperature of −80° C. to 0° C.

11. The production method of the syringe filled with the resin composition according to claim 9,
wherein a time during which the syringe filled with the resin composition is held under the reduced pressure environment is 30 minutes or more.

12. The production method of the syringe filled with the resin composition according to claim 9,
wherein a filling amount of the resin composition into the syringe barrel is 10% to 95% of an internal capacity of the syringe.

* * * * *